(12) United States Patent
Doris et al.

(10) Patent No.: US 9,839,700 B2
(45) Date of Patent: Dec. 12, 2017

(54) POLYMERIZED MICELLES FOR DIAGNOSIS

(75) Inventors: Eric Doris, Orsay (FR); Frédéric Ducongé, Sceaux (FR); Edmond Gravel, L'haÿ les Roses (FR); Nicolas Mackiewicz, Suisse MN (FR); Bertrand Tavitian, Paris (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 914 days.

(21) Appl. No.: 13/816,414

(22) PCT Filed: Jul. 7, 2011

(86) PCT No.: PCT/IB2011/053025
§ 371 (c)(1),
(2), (4) Date: Mar. 5, 2013

(87) PCT Pub. No.: WO2012/020337
PCT Pub. Date: Feb. 16, 2012

(65) Prior Publication Data
US 2013/0230467 A1 Sep. 5, 2013

(30) Foreign Application Priority Data
Aug. 9, 2010 (EP) ...................... 10290440

(51) Int. Cl.
*A61K 9/00* (2006.01)
*A61K 49/00* (2006.01)
*A61K 9/107* (2006.01)

(52) U.S. Cl.
CPC ........ *A61K 49/0082* (2013.01); *A61K 9/1075* (2013.01); *A61K 49/0032* (2013.01); *A61K 49/0054* (2013.01)

(58) Field of Classification Search
CPC .................................. A61K 49/0082
See application file for complete search history.

(56) References Cited

U.S. PATENT DOCUMENTS 5,512,294 A * 4/1996 Li ...................... A61K 49/1812
424/1.21
6,306,598 B1 10/2001 Charych et al.
(Continued)

FOREIGN PATENT DOCUMENTS

WO  WO 02/100439    12/2002
WO  WO 2005/058376   6/2005
(Continued)

OTHER PUBLICATIONS

Adams et al., "Comparison of visible and near-infrared wavelength-excitable fluorescent dyes for molecular imaging of cancer", J. Biomed Opt. (2007), vol. 12, No. 2, p. 024017 (Abstract Only).
(Continued)

*Primary Examiner* — Paul Dickinson
(74) *Attorney, Agent, or Firm* — Hunton & Williams LLP (57) ABSTRACT

The invention relates to polymerized micelles of size inferior to 100 nm for in vivo diagnosis, in particular of cancer. The polymerized micelles of the invention comprise a diagnostic agent and an amphiphilic polymer obtainable by the polymerization of an amphiphilic monomer, said monomer comprising: a lipophilic chain comprising a polymerizable vinylic or diacetylenic group, and a hydrophilic head comprising a polyoxyethylene or polyoxypropylene chain. The invention finds application in the pharmaceutical field, in particular.

16 Claims, 7 Drawing Sheets

(56) References Cited

U.S. PATENT DOCUMENTS

| | | | |
|---|---|---|---|
| 2002/0071843 A1* | 6/2002 | Li | A61K 49/0002 424/155.1 |
| 2005/0003008 A1* | 1/2005 | Rapoport | A61K 9/1075 424/486 |
| 2007/0275371 A1 | 11/2007 | Sim et al. | |

FOREIGN PATENT DOCUMENTS

| | | |
|---|---|---|
| WO | WO 2005/120585 | 12/2005 |
| WO | WO 2006/113666 | 10/2006 |
| WO | WO 2008/124634 | 10/2008 |
| WO | WO 2009/133325 | 11/2009 |

OTHER PUBLICATIONS

Dhar et al., "Targeted delivery of cisplatin to prostate cancer cells by aptamer functionalized Pt(IV) prodrug-PLGA-PEG nanoparticles", PNAS (2008), vol. 105, No. 45, pp. 17356-17361.

Faure et al., "Control of the in vivo biodistribution of hybrid nanoparticles with different poly(ethylene glycol) coatings", Small (2009), vol. 5, No. 22, pp. 2565-2575 (Abstract Only).

Gao et al., "Ultrasmall Near-infrared Non-cadmium Quantum Dots for in vivo Tumor Imaging", Small (2010), vol. 6, No. 2, pp. 256-261.

Garofalakis et al., "In vivo validation of free-space fluorescence tomography using nuclear imaging", Opt. Lett. (2010), vol. 35, No. 18, pp. 3024-3026 (Abstract Only).

Itoh et al., "Photo-Induced Dimer-Diradical Formation in Diacetylene Crystals at Low Temperatures", Journal of the Physical Society of Japan (1999), vol. 68, No. 5, pp. 1711-1715.

Kollmar, C., "Electronic Structure of Diradical and Dicarbene Intermediates in Short-Chain Polydiacetylene Oligomers", J. Chem. Phys. (1993), vol. 98, pp. 7210 (Abstract Only).

Lammers et al., "Tumour-targeted nanomedicines: principles and practice", British Journal of Cancer (2008), vol. 99, pp. 392-397.

Larsen et al., "Size-Dependent Accumulation of PEGylated Silane-Coated Magnetic Iron Oxide Nanoparticles in Murine Tumors", ACS Nano (2009), vol. 3, No. 7, pp. 1947-1951 (Abstract Only).

Lee et al., "All-in-one target-cell-specific magnetic nanoparticles for simultaneous molecular imaging and siRNA delivery", Angew Chem. Int. Ed. Eng. (2009), vol. 48, No. 23, pp. 4174-4179 (Abstract Only).

Ntziachristos et al., "Fluorescence imaging with near-infrared light: new technological advances that enable in vivo molecular imaging", Eur. Radiol. (2003), vol. 13, pp. 195-208.

Ogier et al., "Recent advances in the field of nanometric drug carriers", Future Med. Chem. (2009), vol. 1, No. 4, pp. 693-711 (Abstract Only).

Ogier et al., "Enhanced drug loading in polymerized micellar cargo", Org. Biomol. Chem. (2010), vol. 8, No. 17, pp. 3902-3907 (Abstract Only).

Okawa et al., "Linear chain polymerization initiated by a scanning tunneling microscope tip at designated positions", J. Chem. Phys. (2001), vol. 115, p. 2317 (Abstract Only).

Owens et al., "Opsonization, biodistribution, and pharmacokinetics of polymeric nanoparticles", Int. J. Pharm. (2006), vol. 307, No. 1, pp. 93-102 (Abstract Only).

Peer et al., "Nanocarriers as an emerging platform for cancer therapy", Nature Nanotechnology (2007), vol. 2, pp. 751-760 (Abstract Only).

Perrault et al., "Mediating tumor targeting efficiency of nanoparticles through design", Nano Lett. (2009), vol. 9, No. 5, pp. 1909-1915 (Abstract Only).

Pluen et al., "Role of tumor-host interactions in interstitial diffusion of macromolecules: Cranial vs. subcutaneous tumors", PNAS (2001), vol. 98, No. 8, pp. 4628-4633.

Sixl et al., "Theory of the radical-electron configurations and optical excitations in short-chain polydiacetylene oligomers", Phys. Rev. B Condens. Matter (1987), vol. 36, No. 5, pp. 2747-2756 (Abstract Only).

Tang et al., "Shell-detachable micelles based on disulfide-linked block copolymer as potential carrier for intracellular drug delivery", Bioconjug. Chem. (2009), vol. 20, No. 6, pp. 1095-1099 (Abstract Only).

Torchilin, VP, "Micellar nanocarriers: pharmaceutical perspectives", Pharm. Res. (2007), vol. 24, No. 1, pp. 1-16 (Abstract Only).

Wei et al., "Preparation of Hierarchical Hollow $CaCO_3$ Particles and the Application as Anticancer Drug Carrier", J. Am. Chem. Soc. (2008), vol. 130, No. 47, pp. 15808-15810.

Yang et al., "Long-Circulating Near-Infrared Fluorescence Core-Crosslinked Polymeric Micelles: Synthesis, Characterization, and Dual Nuclear/Optical Imaging", Biomacromolecules (2007), vol. 8, No. 11, pp. 3422-3428.

Zhang et al., "HDL-mimicking peptide-lipid nanoparticles with improved tumor targeting", Small (2010), vol. 6, No. 3, pp. 430-437 (Abstract Only).

Larock, R.C., "Comprehensive Organic Transformations", (2nd Ed., 1999) (VCH Publishers) (Table of Contents only, 30 pp).

International Search Report for PCT/IB2011/053025 dated Oct. 21, 2011.

Written Opinion of the International Searching Authority for International Patent Application PCT/IB2011/053025 dated Feb. 9, 2013.

Choi Hye et al, "Synthesis of poly(ethylene glycol)-polydiacetylene conjugates and their micellar and chromic characteristics," Journal of Nanoscience and Nanotechnology, LNKD-PUBMET:19198400, vol. 8, No. 10, pp. 5104-5108, Oct. 2008.

Nurunnabi, M et al, "Targeted near-IR QDs-loaded micelles for cancer therapy and imaging," Biomaterials, vol. 31, No. 20, pp. 5436-5444, Jul. 2010.

* cited by examiner

POLYMERIZED MICELLES FOR DIAGNOSIS

CROSS-REFERENCE TO RELATED APPLICATIONS

This is the U.S. National Stage application of International Patent Application No. PCT/IB2011/053025, filed Jul. 7, 2011, which claims priority to EP 10 290440.6, filed Aug. 9, 2010, the disclosure of which is hereby incorporated by reference in its entirety.

The present invention relates to polymerized micelles, their method of preparation as well as their use in diagnosis, notably in the diagnosis of cancer, in particular by tumor imaging.

In recent years, nanoparticles have attracted the attention of researchers in many different domains, and particularly in the medical field. Their use as potential diagnostic or therapeutic tools for cancer research has been the subject of several recent surveys that have yielded highly promising results.[1, 2, 3, 4, 5, 6]

For diagnosis and treatment monitoring by non-invasive in vivo tumor imaging, near infrared (NIR) imaging stands as one the most convenient techniques.[7, 8] NIR fluorescent light (L e. 700-1000 nm) exhibits very little interaction with biological tissues (low absorbance and usually negligible auto-fluorescence) inside which it can penetrate as deep as several centimeters.[9, 10]

The successful use of a nanocarrier for tumor imaging and drug delivery is closely related to its biodistribution and generally hinges on the enhanced permeation and retention (EPR) effect.[11] The EPR effect is the result of passive diffusion of nanometric objects through blood vessels that irrigate the tumor. These so-called neovessels have looser endothelial inter-cellular junctions, due to their inflammatory nature, and are much more permeable than ordinary vessels. Thus, these blood vessels are usually pierced by wide pores of size ranging from 100 nm to 2 μm, depending on the type of tumor. In addition, lymphatic drainage of the tumor is poorly efficient, hence allowing objects to remain longer once they have diffused inside the tumor tissues.

The aptitude of a nanoparticle to achieve passive targeting of tumor cells via EPR effect depends mainly on its size (to allow interstitial diffusion from the blood)[12] and surface chemistry (to permit longer blood circulation).

Several nanoparticulate systems in the 70-200 nm size range have been explored for cancer targeting by the EPR effect including liposomes, dendrimers, ceramic or metallic nanoparticles, carbon nanotubes, and micelles.[13a, 13b, 11].

However, recent studies suggested that particles of smaller sizes (ie. <30 nm) might better diffuse through blood vessel walls and reach deeper tumor tissues.[13c, 13d]

Among nanoparticles, micelles are good candidates for medical applications as they are easily synthesized within an appropriate size range (i.e. <30 nm) in a reproducible manner, from non-toxic materials (as opposed to other nanoparticles like quantum dots, for instance). However, two major drawbacks hinder their use: they usually have short circulation half-lives and limited cargo-shielding (unstable drug retention).[13, 14]

Recently, polymerized micelles resulting from the polymerization of amphiphilic molecules of type PDA-NTA, which structure is represented below, have been disclosed in the international patent application WO 2009/133325. These polymerized micelles can be loaded with hydrophobic active substances and are used as nanovectors. However, no mention is made of any EPR effect.

PDA-NTA

It now has been discovered novel micellar nanoparticles that address the aforementioned problems and which are particularly useful for tumor imaging. More specifically, the invention provides polymerized micelles which are non toxic and display significant tumor accumulation through enhanced permeation and retention (EPR) effect. Further, they advantageously exhibit satisfactory blood residence time, tumor uptake and imaging contrast. In addition, these polymerized micelles exhibit satisfactory drug loading capacity and cargo-shielding. Furthermore, unexpectedly, it has been shown that the polymerized micelles according to the invention exhibit improved properties, notably an enhanced EPR effect, as compared to those disclosed in the prior art, and in particular to PDA-NTA.

As a further advantage, contrary to a large number of nanoparticles, the synthesis of the polymerized micelles according to the invention is easily controllable and reproducible, as well as economical.

Thus, according to a first objet, the invention is directed to a polymerized micelle of size inferior to 100 nm for use in in vivo diagnosis, said polymerized micelle comprising:
a diagnostic agent, and
an amphiphilic polymer obtainable by the polymerization of an amphiphilic monomer, said monomer comprising:
a lipophilic chain comprising a polymerizable vinylic or diacetylenic group allowing the polymerization of the micelle, and
a hydrophilic head comprising a polyoxyethylene or polyoxypropylene chain.

In a preferred aspect, the invention provides polymerized micelles for use in cancer diagnosis, in particular by tumor imaging.

As used herein, the term "micelle" refers to a spherical aggregate of amphiphilic molecules dispersed in a liquid colloid, notably in water, and which size, more specifically the hydrodynamic diameter is inferior to 100 nm, preferably inferior to 80 nm, notably to 60 nm, more preferably below 30 nm, most preferably of about 10 nm, as measured by Dynamic Light Scattering. Thus, as used herein, the term "micelle" refers to a core-shell structure composed of a monolayer of amphiphilic molecules, wherein in aqueous media, the shell is composed of the "hydrophilic head" regions of said amphiphilic molecules, and the core is composed of the hydrophobic tail regions of the amphiphilic molecules. This type of micelle is known as a normal phase micelle (also called oil-in-water micelle). Inverse micelles, also called water-in-oil micelles, have the hydrophilic heads at the centre with the hydrophobic tails extending out. Preferably, micelles suitable according to the present invention are oil-in-water micelles. As used herein, the term micelle thus does not include any supramolecular assembly composed of a bilayer of amphiphilic molecules such as vesicles or liposomes.

As used herein, the term "amphiphilic" means an organic molecule, also called a surfactant, possessing both hydrophilic and lipophilic properties. Amphiphilic compounds or surfactants thus comprise or consist of two distinct hydrophobic and hydrophilic domains. Upon dispersion in aqueous media, spontaneous phase separation occurs, leading to supra-molecular core-shell micelle structure. The core is constituted by the hydrophobic region of the amphiphilic polymer and is shielded from water by the hydrophilic outer shell (hydrophilic heads). The self assembly is dependent on concentration and temperature. At lower concentrations, amphiphilic monomers are individualized species. As the concentration increases, the monomers self organize into micelles when the critical micellar concentration (CMC) is reached. The formation of the micelles is also dependent on the temperature and, more precisely, on the critical micellar temperature.

Amphiphilic compounds or surfactants are also often classified into four primary groups: anionic, cationic, non-ionic, and zwitterionic (dual charge). In a preferred aspect of the invention, the amphiphilic compound is cationic or non-ionic, more preferably non-ionic.

Amphiphilic monomers described herein comprise a polymerizable unit. This reactive function allows micelle polymerization. Thus, upon UV irradiation at 254 nm, diacetylenes undergo polymerization via a topochemical 1,4-addition mechanism[14a-14d]. This polymerization enables to strengthen the micellar architecture and to preserve the integrity of the structure even in a dilute medium, when the concentration is inferior to the CMC.

Amphiphilic Monomer

In a preferred aspect, the amphiphilic monomer is a monomer consisting of:
a lipophilic chain comprising a polymerizable vinylic or diacetylenic group, whose polymerization leads to the polymerization of the micelle, and
a hydrophilic head comprising a polyoxyethylene or polyoxypropylene chain.

In a preferred aspect, the hydrophilic head comprises or consists of a polyoxyethylene (PEG) chain, preferably having a molecular weight in the range of 300 to 10000 g. mol$^{-1}$, more preferably in the range of 1000 to 5000 g. mol$^{-1}$. The molecular weight ratio of the PEG relative to the lipophilic chain of the amphiphilic monomer ranges from 1 to 30.

Indeed, PEG chains are known to be biocompatible (little to no toxicity and immunogenicity) and to limit interaction of PEG-coated particles with plasma proteins and especially with opsonins often responsible for phagocytosis by macrophages, hence diminishing their recognition by cells of the reticulo-endothelial system (RES).[15]

In a further aspect, the amphiphilic monomer is a monomer of formula (I):

$$X\text{-}L_0\text{-}[L_1\text{-}Y]_k\text{-}L_2$$

Wherein:
X is —$(CH_2$—$CH_2$—$O)_n$—Z;
Y is —C≡C—C≡C—;
$L_0$ is a bond, —O—C(=O)—, —$NR_3$—C(=O)—, —O—C(=S)—, —$NR_3$—C(=S)—, —O—, —$NR_3$—;
$L_1$ is at each occurrence —$(CH_2)_p$—;
$L_2$ is —$(CH_2)_q$—$CH_3$;
Z is H, or —$(CH_2)_m R_1$,
$R_1$ is H, $COOR_2$, SH, maleimidyl, $NH_2$, $N_3$ or C≡CH;
$R_2$ and $R_3$ are each independently selected from H, $C_1$-$C_6$ alkyl;
m is an integer from 1 to 4;
n is an integer from 5 to 230;
k is an integer from 1 to 5;
p is at each occurrence an integer from 1 to 24;

q is an integer from 1 to 24.
Preferably, k is 1 or 2.
Preferably, Z is H or $CH_2$—COOH.
Preferably, n is 8 or 45.
In a preferred variant, the amphiphilic monomer of formula (I) is a monomer of formula (Ia):

Wherein Z is H or $CH_2COOH$, and n, p, q are as defined above.

Most preferably, the amphiphilic monomer is selected from monomers of formula (Ia), wherein:
p is 8,
q is 10,
n is 8 or 45, and
Z is H or $CH_2COOH$.

Preferably, the amphiphilic polymer is obtained by the polymerization of a mixture containing two distinct amphiphilic monomers of formula (I), notably a first amphiphilic monomer wherein Z is H and a second amphiphilic monomer of formula (I) wherein Z is —$(CH_2)_m R_1$.

Diagnostic Agent

As used herein, the expression "in vivo diagnosis" refers to a diagnostic method applied to a human or animal body.

The diagnostic agent can be a substance emitting electromagnetic rays or a substance detectable by X-ray, ultrasound or nuclear magnetic resonance. The polymerized micelles can thus comprise iron oxide particles, such as magnetite or maghemite, gadolinium chelates, radio-opaque materials, such as, for example, air or barium, or fluorescent compounds, such as rhodamine or nile red, or gamma emitters, such as indium or technetium, or positron emitters such as $^{18}F$ or $^{11}C$, or any other radioactive label.

Preferably, the diagnostic agent is a fluorescent compound, such as that sold under the tradename FluoProbes® 730 (FP730) thus, allowing the cancer diagnosis to be carried out by tumor fluorescence imaging.

The diagnostic agent may be either coupled with at least one of the hydrophilic heads at the micelle surface, notably via a covalent bond, directly or via a homo- or heterobifunctional reagent, or loaded in the lipophilic core of the micelle.

Preferably, the diagnostic agent is coupled with at least one of the hydrophilic heads at the micelle surface.

Active Substance

The polymerized micelles herein described may further comprise an active substance. The polymerized micelles may thus be useful as a carrier (vector) of an active substance.

The active substance may be notably hydrophobic.

As used herein, the term "hydrophobic" denotes small organic compounds having a low solubility in water that is inferior to 1 g per litre in all or some pH zones. By extension, this term also includes proteins or nucleic acids having problems of solubility or of stability in an aqueous medium.

Hydrophobic substances will be preferably included inside the hydrophobic core of the micelle, either through covalent linkage with the amphiphilic polymer or solely by hydrophobic interactions with the hydrophobic domain of the amphiphilic polymer.

Covalent coupling of the active substance is usually achieved using a peptidic-type coupling with the hydrophobic segment of the polymer. An alternative to peptidic coupling could be the formation of an acetal or a hydrazone linkage. These bonds are hydrolysable in slightly acidic medium, which induces the release of the drug.

Encapsulation of drugs by hydrophobic interaction with the hydrophobic domain of the amphiphilic polymer can be achieved by conventional methods, in four different ways: direct inclusion by stirring the drug in a polymer micelle solution, inclusion by evaporation, inclusion by dialysis or inclusion using a cosolvent followed by evaporation (nanoprecipitation).

Inclusion of the hydrophobic active substance into the micelle may be performed either before or after the polymerization of the micelle.

As examples of active substances which may be contained in the polymerized micelles of the invention, mention may particularly be made, without limitation, of pharmaceutical, cosmetic, veterinary, phytosanitary products, or processed foodstuffs.

Examples of pharmaceutical products include notably, antipyretics, aspirin and derivatives, antibiotics, anti-inflammatories, antiulceratives, antihypertensives, neuroleptics, anti-depressants, analgesics, antifungics, antiviral, antitumorous agents, immunomodulators, antiparkinsonian, nucleotides, oligonucleotides, peptides, proteins, radionucleides.

Examples of cosmetic active substances include notably self-tanning or anti-UV agents.

Examples of processed foodstuffs are notably vitamins.

Examples of veterinary products include notably hormones, vaccines, anti-inflammatories, antibiotics.

Examples of phytosanitary active substances are notably herbicides, bactericides, fungicides, insecticides, acaricides or regulators of growth.

Targeting Entity

The polymerized micelles herein described may further comprise a targeting entity, notably for enhanced efficacy.

As used herein, "targeting entity" refers to a specific targeting entity, generally a ligand, capable of recognizing specific antigens or receptors on the surface of the targeted cell. This targeting relies, for example, on ligand-receptor, antibody-antigen or lectin-carbohydrate interactions. Accumulation of polymerized micelles on the cell surface is thus made possible using specific targeting. For example, folate or integrin ($\alpha_v\beta_3$ or $\alpha_v\beta_5$) receptors are often overexpressed on tumor cells. Thereby, functionalization of the polymerized micelle with the tripeptide sequence arginine-glycine-aspartic acid (RGD) enables it to specifically recognize integrin $\alpha_v\beta_3$ receptors, whereas folic acid recognizes the folate receptor. Preferred targeting entities are notably peptides, carbohydrates, antibodies, aptamers.

The targeting entity is preferably covalently coupled to the surface of the polymerized micelle, notably to one of the hydrophilic heads of the amphiphilic polymer.

The targeting entity can be grafted on the amphiphilic monomer before or after the micelle has been assembled, before or after the polymerizable groups of the amphiphilic monomers have been polymerized.

Polymerized Micelles

According to another object, the invention provides a polymerized micelle of size inferior to 100 nm comprising an amphiphilic polymer obtainable by the polymerization of an amphiphilic monomer of formula (I) as defined above.

In a further aspect, the polymerized micelle comprises an active substance, notably hydrophobic, included inside its hydrophobic core.

In a particular embodiment, at least one, notably all or some of the groups Z of the polymerized micelle are coupled to a diagnostic agent, either directly via a covalent bond, or indirectly via a homo- or heterobifunctional reagent. By way of illustration, the homobifunctional reagent, glutaraldehyde, may be suitable for carrying out the coupling of a group Z=NH$_2$ with a group —NH$_2$ of the diagnostic agent.

According to a preferred variant, the Z groups form a covalent bond with the diagnostic agent of type —CO—NH—, —NH—CO—, —COO—, —O—CO—, more preferably of type —CO—NH— or —NH—CO—.

As used herein, the expression "all or some" means that not all the Z groups are necessarily coupled to a diagnostic agent, but that the degree of coupling is sufficient for the desired intensity of signal to be obtained.

Amphiphilic Monomer

In another aspect, the invention provides an amphiphilic monomer of formula (I):

X-L$_0$-[L$_1$-Y]$_k$-L$_2$

Wherein X, Y, L$_1$, L$_2$ and k are as defined above, and L$_0$ is a bond, —O—C(=S)—, —NR$_3$—C(=S)—, —O—, —NR$_3$—.

Method of Preparation of the Polymerized Micelles

According to a further object, the invention relates to a method for preparing a polymerized micelle of size inferior to 100 nm as defined above, said method comprising the steps of:

i) self-assembling the amphiphilic monomer as defined above into micelles;

ii) polymerizing the obtained self-assembled micelles; and optionally iii) coupling some or all of the hydrophilic head of the polymerized micelle with a diagnostic agent, or loading it in the core of the micelle.

As used herein, the term "self-assembling" of amphiphilic monomers refers to the spontaneous organization of the amphiphilic monomers into spherical micelles in an aqueous medium at a concentration higher to the critical micelle concentration (CMC).

The polymerization of the self-assembled micelle may be carried out by a photopolymerization or a radical polymerization.

The photopolymerization is a method particularly suitable for the polymerization of diacetylenic motives. The photopolymerization is a "clean" method, requiring a light irradiation at 254 nm and no other external chemical agent. The photopolymerization of diacetylenic motives involves the formation of diradical intermediates: the first step consists in forming the diradical species by a photonic excitation; the second one is the propagation reaction of the radical to a new neighboring polymerizable motive, thereby allowing the polymeric chain to grow; the last step is a termination step by coupling two radicals.

The radical polymerization is particularly suitable for the polymerization of vinylic groups, including acrylate groups. This polymerization route is well known and commonly used. The initiation of radical polymerization can be performed in the presence of a radical initiator generated by a thermal dissociation, oxido-reduction reactions or by irradiations.

The polymerization step ii) may include several types of successive polymerization, for example a photopolymerization followed by a radical polymerization.

In a preferred embodiment, the obtained auto-assembled micelles are photopolymerized.

Method of Preparation of the Amphiphilic Monomers

The amphiphilic monomers of the present invention may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art.

In particular, such methods can be found in R. C. Larock, *Comprehensive Organic Transformations*, VCH publishers, 1989.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

Thus, according to a further object, the invention relates to a method for preparing an amphiphilic monomer as defined above, said method comprising:

reacting a compound of formula W-[$L_1$-Y]$_k$-$L_2$,
wherein
W is selected from Hal, Hal-$CH_2$—, Cl—C(=O)—, HO—C(=O)—, Cl—C(=S)—, HO—C(=S)—, Hal being an halogen atom,
with a polyoxyethylene or polyoxypropylene chain of formula H—(O—CW—$CH_2$)$_n$—OH or H—(O—$CH_2$—CH($CH_3$))$_n$—OH in the presence of a base in a solvent; and optionally
reacting the obtained compound with a compound Hal-($CH_2$)$_m$R, wherein Hal is an halogen atom, in the presence of a base in a solvent; and optionally
recovering the obtained amphiphilic monomer.

In a further aspect, the compound Hal-[$L_1$-Y]$_k$-$L_2$ is prepared from the corresponding compound HO-[$L_1$-Y]$_k$-$L_2$. This reaction may be performed by applying well-known methods, for example in the presence of $CBr_4$ and $PPh_3$ in dichloromethane.

In yet a further aspect, the compound HO-[$L_1$-Y]$_k$-$L_2$ is prepared by reduction of the corresponding carboxylic acid HOOC—[($CH_2$)$_{p-1}$Y]$_k$-$L_2$. Generally, this reaction is carried out in the presence of a reducing agent, such as $LiAlH_4$ in a solvent, such as $Et_2O$.

Diagnostic Composition

According to another object, the invention concerns a diagnostic composition, in particular a composition for in vivo diagnosis, comprising a polymerized micelle as defined above, optionally in admixture with one or more pharmaceutically acceptable excipients.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

The diagnostic compositions according to the present invention may be administered parenterally, preferably administrated intravenously. The pharmaceutical forms acceptable for injectable use include, for example, sterile micellar aqueous solutions or dispersions. Aqueous carriers include mixtures of alcohols and water, buffered media, and the like. Nonaqueous solvents include alcohols and glycols, such as ethanol, and polyethylene glycols. The parenteral preparations can be enclosed in ampules, disposable syringes or multiple dose vials.

The invention is further illustrated but not restricted by the description in the following examples.

EXAMPLES

1. Preparation and Characterization of Micelles

Three types of micelles were synthesized and studied: the previously described PDA-NTA micelle, [16] and two new polydiacetylene-based micelles with poly(ethylene glycol) outer regions referred to as PDA-PEG350 and PDA-PEG2000 micelles, with respect to PEG length.

1.1. Chemical Synthesis of Amphiphilic Monomer Units

PDA-NTA micelles result from the self-assembly of a single amphiphilic monomer 1 which was synthesized according to the previously reported protocol (Scheme 1).[16]

Scheme 1. Structure of compound 1

PDA-PEG350 and PDA-PEG2000 micelles are composed of a mixture of two amphiphilic monomers 2 and 3. The general synthesis procedure, depicted in Scheme 2, starts from pentacosa-10,12-diynoic acid 4 which is first reduced into hydroxyl 5. An Appel halogenation reaction permits the formation of the corresponding bromide 6 which is then reacted with polyethylene glycol in presence of sodium hydride to yield either 2a or 2b, depending on PEG length. Deprotonation of 2a or 2b with sodium hydride and reaction with 2-bromoacetic acid 7 give rise to carboxylic acids 3a or 3b respectively.

1). To assemble PDA-PEG2000 micelles, the same protocol was reproduced with the appropriate monomers (2b and 3b).

The degree of polymerization was controlled by UV absorption at 292 nm and more than 75% conversion was observed after 5 hours of irradiation. At that point, all three solutions had turned from colorless to yellowish.

The obtained micelles were characterized by dynamic light scattering (DLS) which gave mean diameters of 6.4, 7.8 and 12.6 nm for PDA-NTA, PDA-PEG350 and PDA-PEG2000 micelles, respectively.

2. In Vivo Behavior and Tumor Imaging

Figure 1:
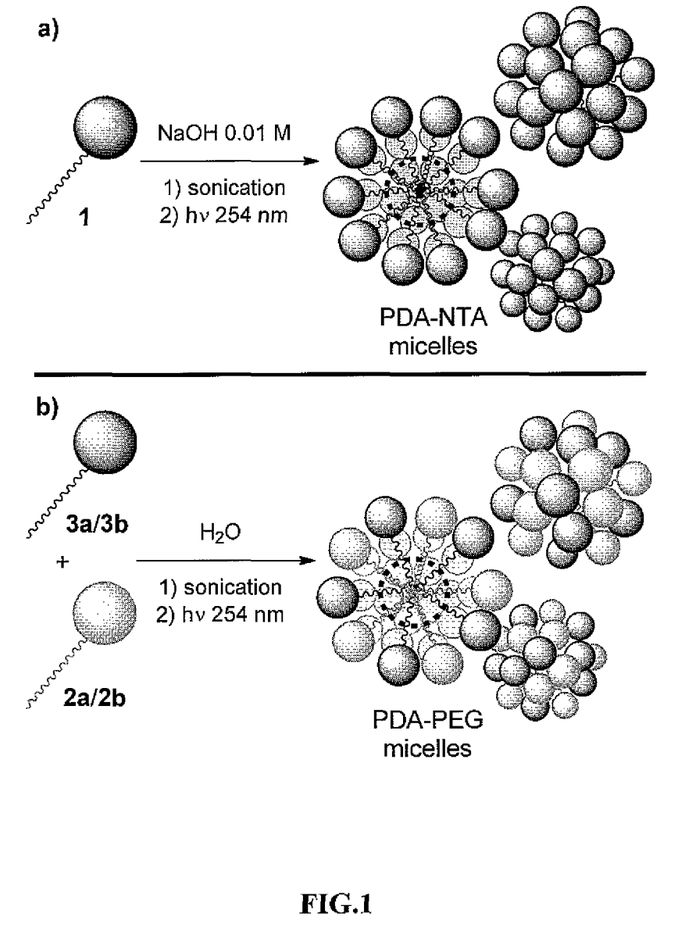
FIG. 1: Assembly of PDA-NTA and PDA-PEG micelles

Scheme 2. Synthetic route to compounds 2a/2b and 3a/3b 1.2. Micelle Assembly and Characterization For the assembly of PDA-NTA micelles, a solution of compound 1 in aqueous sodium hydroxide was sonicated with an ultrasonic probe. The solution was then submitted to UV light (254 nm) irradiation, in order to achieve polymerization of the diacetylene motives and stabilize the micelles and the pH value was adjusted to 7 (FIG. 1).

For the assembly of PDA-PEG350 micelles, equivalent quantities of 2a and 3a were dissolved in deionized water. The solution was then sonicated and irradiated under conditions identical to those used for PDA-NTA micelles (FIG.

2.1. Blood Kinetics and In Vivo Stability of PDA Micelles.

In order to explore their in vivo behavior, micelles were conjugated with NIR emitting FluoProbes® 730 (FP730). The conjugation was performed via peptide coupling between the primary amine of the fluorophore and carboxylic groups at the surface of the micelles.

Figure 2:
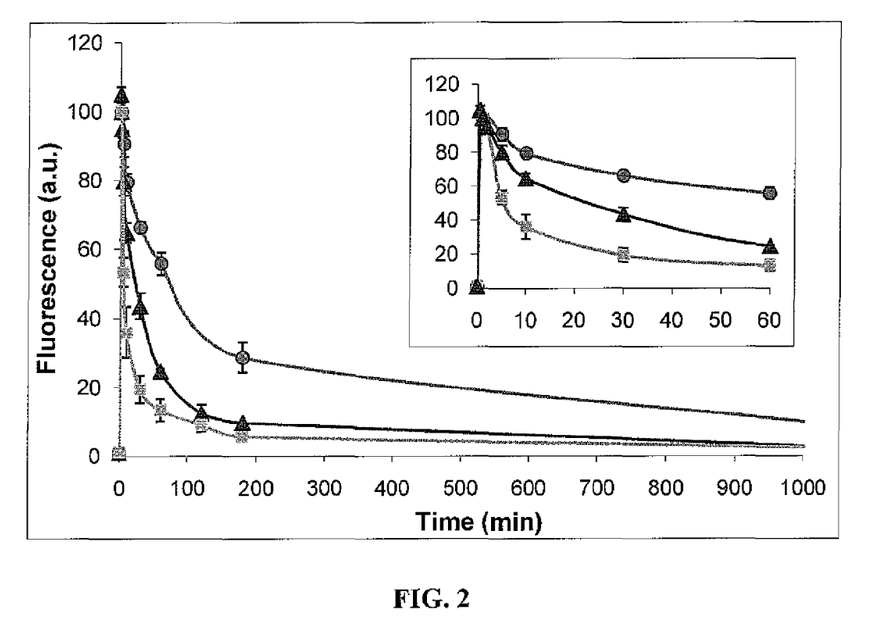
FIG. 2: Kinetics representing the evolution of PDA-PEG2000-FP730 (●), PDA-PEG350-FP730 (▲) and PDA-NTA-FP730 (▩) micelle concentrations in blood.

Blood kinetics of the different micelles were first investigated in nude mice by injection in the caudal vein at a dose corresponding to 1 nmol of fluorescence. Blood samples were collected over time by retro-orbital bleeding and fluorescence was measured at 732 nm (FIG. 2). Within the first hour after injection, a clear difference was observed between the three types of micelles. The fluorescence of PDA-NTA-FP730 micelles decreased abruptly to reach 35% after 10 minutes and was as low as 15% after an hour. The fluorescence of PDA-PEG350-FP730 also decreased quite steadily but was still at almost 65% after 10 minutes and went down to 30% after an hour. In the case of PDA-PEG2000-FP730 micelles, the fluorescence was much more stable and about 65% still remained after the first hour. On a longer time scale, the fluorescence behaviors of PDA-PEG350-FP730 and PDA-NTA-FP730 micelles were very similar, less than 10% remained after 4 hours and after less than a day, virtually all fluorescence had vanished from the blood circulation. On the contrary, the decrease of fluorescence of PDA-PEG2000-FP730 micelles was much slower, with over 25% left after 4 hours and more than 15% remaining after one day.

PEG coatings are known to enhance blood residence time and their positive effect is clearly illustrated by these results. Early kinetics show a superior behavior of PEG-coated micelles over the NTA-coated ones, whereas long term kinetics highlight the benefit of a longer PEG chain as regards blood residence time.

Collected blood samples were also used to study the in vivo stability of the PDA micelles using electrophoresis in a non-denaturing agarose gel. As references, micelles were diluted either in PBS or plasma just before electrophoresis. The electrophoretic mobility of the reference micelles was different in plasma in comparison to PBS. This can be explained by a difference in salt concentration or interaction of the micelles with plasma proteins. Nevertheless, micelles collected from blood samples have the same migration profile as the corresponding plasma references, demonstrating high stability in vivo.

2.2. In Vivo Distribution Behavior and Tumor Targeting of PDA Micelles.

The FP730-labelled micelles were then administered to mice bearing subcutaneous tumors by injection in the caudal vein at a dose corresponding to 1 nmol of fluorescence and distribution of the objects in the whole body of the animals was monitored using planar NIR imaging.

Figure 3:
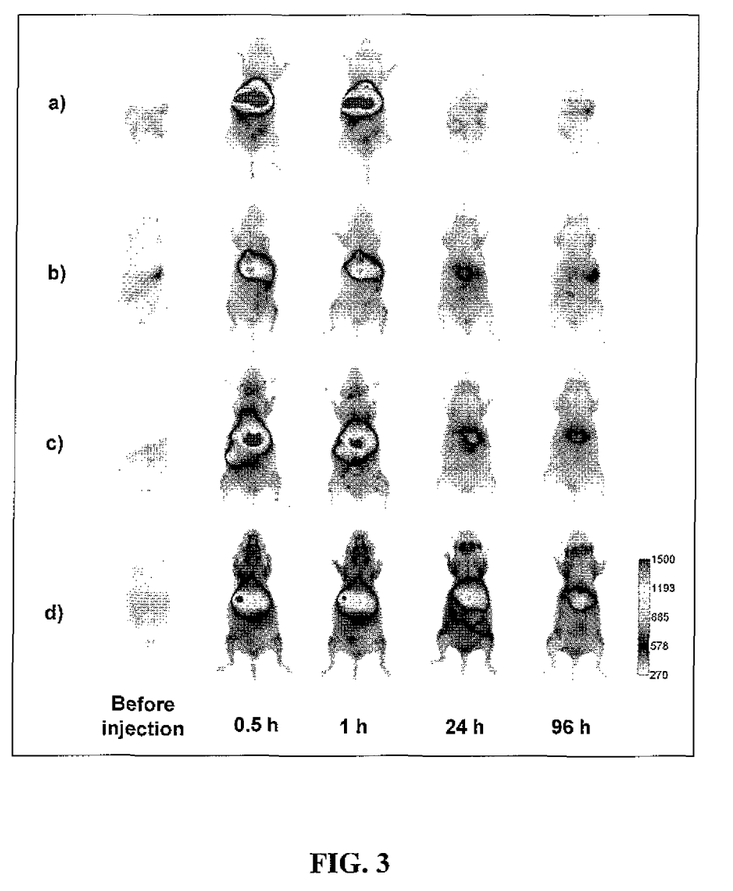
FIG. 3: Biodistributions of a) FluoProbes® 730 alone, b) PDA-NTA-FP730 micelles, c) PDA-PEG350-FP730 micelles and d) PDA-PEG2000-FP730 micelles after IV injection in mice bearing MDA-MB-231 tumors. Ventral side comparison.

For all three micelle types, ventral side observation by planar NIR imaging (FIG. 3) showed high fluorescence in the liver after a few minutes post-injection which decreased as time elapsed. These observations reflect a hepato-biliary excretion route that was rather intense during the first hour and almost totally extinct after one day with PDA-NTA (FIG. 3b) and PDA-PEG350 micelles (FIG. 3c) but still observable for several days in the case of PDA-PEG2000 micelles (FIG. 3d), which is in good accordance with blood kinetics results. By contrast, FluoProbes® 730 injected alone in identical conditions was totally eliminated within a few hours by a similar route (FIG. 3a).

With all micelle types, dorsal side observation by planar NIR imaging (FIG. 4) showed passive accumulation in tumor tissues which is most likely due to EPR effect.

Figure 4:
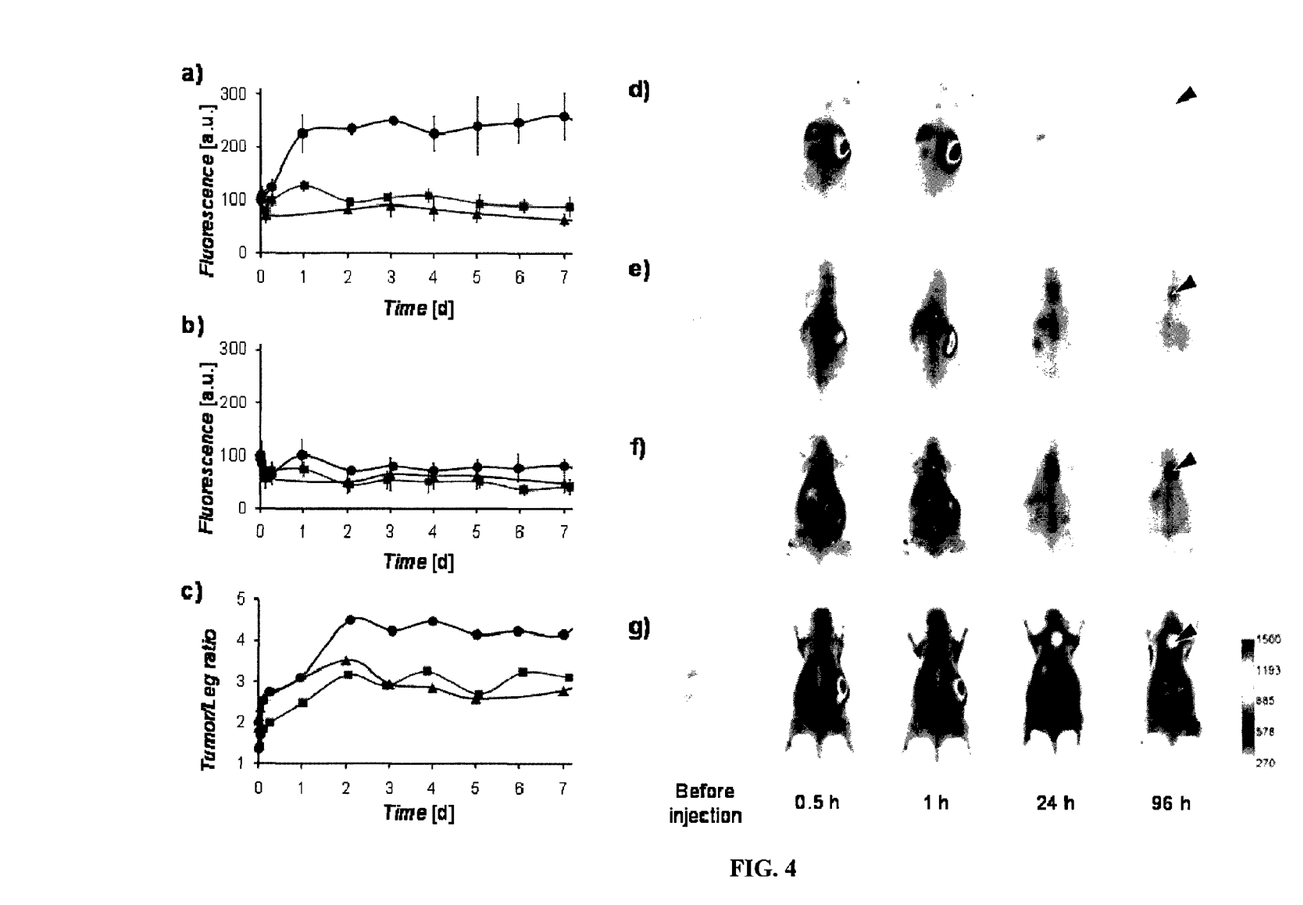
FIG. 4: Results of planar NIR imaging obtained after IV injection in mice bearing MDA-MB-231 xenografts. Evolution of the uptake of PDA-PEG2000-FP730 (●), PDA-PEG350-FP730 (▲) and PDA-NTA-FP730 (▩) micelles in a) tumor and b) leg, normalized at 100 for the time just after injection and taking into account the exposition time and the quenching of fluorescence. c) Ratio of tumor fluorescence signal compared to leg fluorescence signal. Biodistributions of d) FluoProbes® 730 alone, e) PDA-NTA-FP730 micelles, f) PDA-PEG350-FP730 micelles and g) PDA-PEG2000-FP730 micelles after IV injection in mice bearing MDA-MB-231 tumors. Dorsal side comparison

The fluorescence uptake in the tumor and in the leg of the animal are presented in FIGS. 4a and 4b respectively, and FIG. 4c displays the tumor to leg signal ratio which reflects the contrast between the tumor and the rest of the animal's body.

It is known that for a nanoparticle of appropriate size (it appears that sizes below 30 nm are optimal)[12] the longer the blood residence time is, the better the passive accumulation by EPR effect will be. The latter assumption is strongly corroborated by the results obtained in this study. In fact, while the three types of micelles are all in the adapted size range, as testified by the actual tumor accumulation found with all of them, PDA-PEG2000 micelles clearly stand out in terms of both contrast with the whole body and fluorescence intensity.

The behaviors of PDA-NTA and PDA-PEG350 micelles are quite comparable, with little tumor uptake and contrast after 24 hours. On the contrary, PDA-PEG2000 micelles showed strong and persistent tumor uptake after 24 hours with maximum contrast after 48 hours which remained constant for more than a week.

To quantify tumor uptake of PDA-PEG2000 micelles, free space fluorescence diffuse optical tomography (fDOT) was used. The inventors recently calibrated this technique using nuclear imaging and demonstrated that it can be used for non-invasive quantification of the concentration of fluorescent probes in small animals.[17] One day after injection, the tumor uptake of PDA-PEG2000-FP730 was measured around 2.7±1.9% of injected dose. During this experiment, [$^{18}$F]-fluorodeoxyglucose ([$^{18}$F]-FDG) was injected 24 h after PDA-PEG2000-FP730 and localization of micelles was compared to the tumor imaging by [$^{18}$F]-FDG using positron emission tomography (PET). [$^{18}$F]-FDG is a well-validated PET tracer in oncology that is trapped by cancer cells in proportion to their glycolytic activity. This experiment showed that 40±19% of the retained micelles were co-registered with the tumor volume visualized by FDG, with predominant localization in the highly vascularized lower part, reflecting their good diffusion in the tumor. Additionally, fDOT imaging alone was performed over several days and confirmed retention of the micelles in tumors. As the distribution appeared to be favorable, passive drug delivery properties of the micelles were explored.

3. Drug Delivery Potential Assessment

Based on the above results, PDA-PEG2000 micelles appeared to be the best candidates for drug delivery applications, considering their longer blood circulation residence time (which should result in a better bioavailability of the carried drug) and better overall accumulation in tumors (in terms of selectivity and quantity).

For preliminary investigations regarding the potential use of PDA-PEG2000 micelles as drug cargos, paclitaxel (PTX), a hydrophobic molecule with high anticancer activity (active compound of Taxol®) was chosen as a test compound.

A prerequisite for the delivery of a drug is its loading and retention inside the carrier. To assess this feature, loading experiments were first conducted using the protocol previously described for PDA-NTA micelles involving the agitation of the drug suspended in a solution of polymerized micelles at 50° C. for 12 hours. This loading method led to no paclitaxel loading in the case of PDA-PEG2000 micelles, probably because of the thick hydrophilic PEG shell that forbade passage of the hydrophobic drug towards the micelle's core, in contrast with the ionic surface of PDA-NTA micelles.[16]

Encapsulation was made possible by generating the micelles in conditions similar to those described above (cf. 1.2.) in the presence of an excess of suspended paclitaxel. Reproducible results obtained by this technique were measured by mass-balance, demonstrating a 10% w/w (ca. 30% mol/mol) loading of paclitaxel in PDA-PEG2000 micelles. This encapsulation technique is suitable for virtually any therapeutic molecule since it requires neither extended contact with water nor prolonged heating. Solutions of loaded PDA-PEG2000 micelles appeared to be very stable and no precipitate was observed after storage for more than two months at 8° C.

Figure 5:
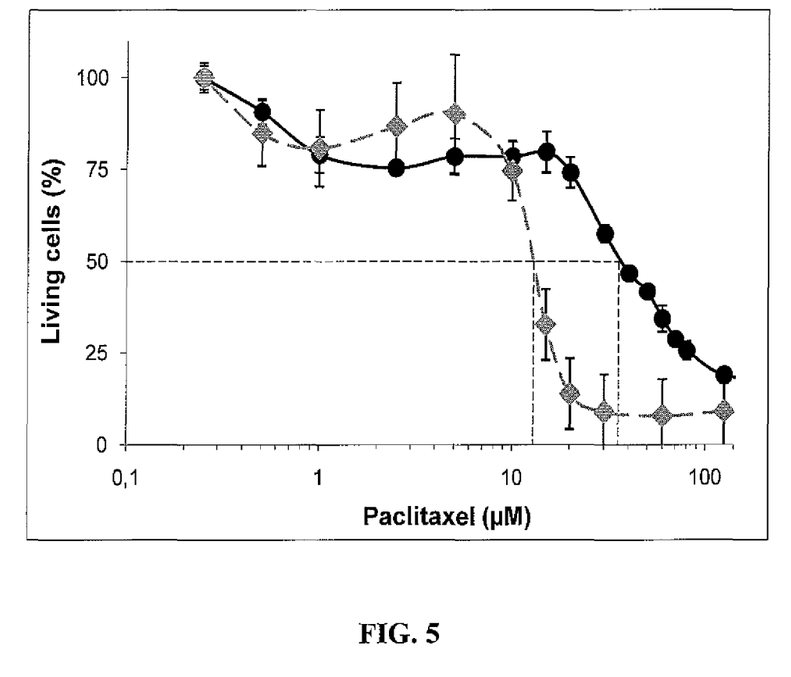
FIG. 5: In vitro cytotoxicity of PDA-PEG2000-PTX micelles (●) and Taxol® (✦) on MDA-MB-231 cells. Experiment performed with CellTiter 96® AQ$_{ueous}$ One Solution Cell Proliferation Assay (Promega)

To assess whether the encapsulated drug retains its therapeutic activity within the polymerized micelles, in vitro assays were carried out. The cytotoxicity of the PTX-loaded PDA-PEG2000 micelles on MDA-MB-231 cells was compared to that of commercially formulated Taxol®. As shown in FIG. 5, comparable $IC_{50}$ were obtained for both formulations (ca. 12 µM for Taxol® and 35 µM for PTX-loaded micelles), demonstrating that paclitaxel remains active even when encapsulated in the micellar cargo. In parallel, the empty cargo was also evaluated and showed no toxicity.

To further confirm the aptitude of PDA-PEG2000 micelles to be used as drug carriers in vivo, their distribution and accumulation were monitored in conditions reproducing a typical tumor regression experiment. During one month, PDA-PEG2000-FP730 micelles were administered to mice bearing MDA-MB-231 tumors by intra-peritoneal (IP) injection on a semiweekly basis. After tumors were established, mice (n=4 per group) were treated with PTX-loaded PDA-PEG2000 micelles ([PTX]=5 mg kg$^{-1}$), Taxol® ([PTX]=5 mg kg$^{-1}$), and physiological serum by intraperitoneal (IP) injection twice a week during 8 weeks.

As seen in previous experiments, tumor uptake by EPR effect was observed as soon as 24 hours after the first injection. The accumulation was maintained and strengthened by repeated doses to reach a maximum after the sixth injection, and was constant for the remainder of the experiment.

Figure 6:
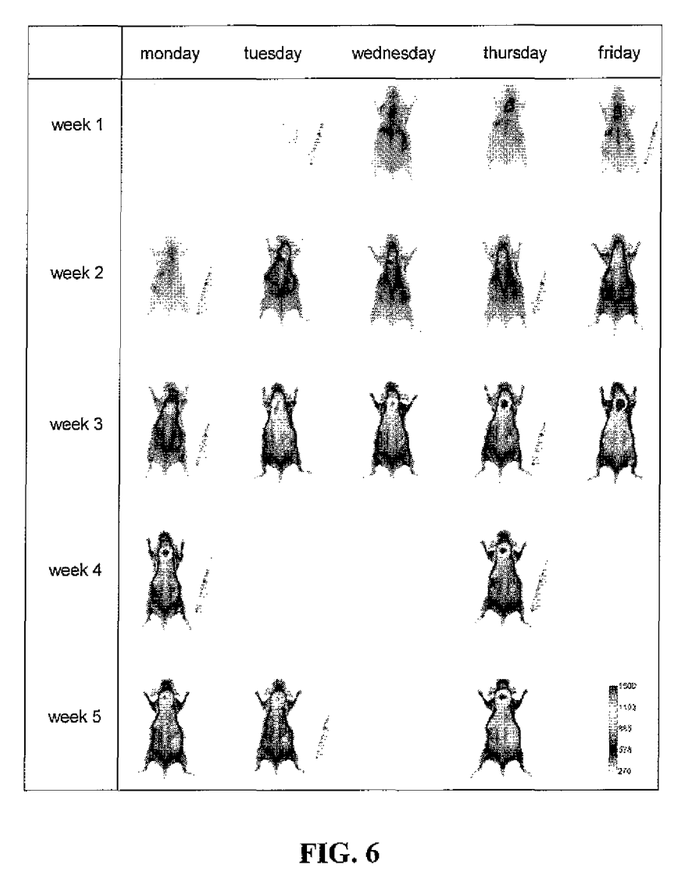
FIG. 6: Planar NIR imaging of an MDA-MB-231 tumor-bearing mouse subjected to repeated IP injections of PEG2000-730-FP730 micelles (twice a week over one month). Syringes mark days of injection.
Figure 7:
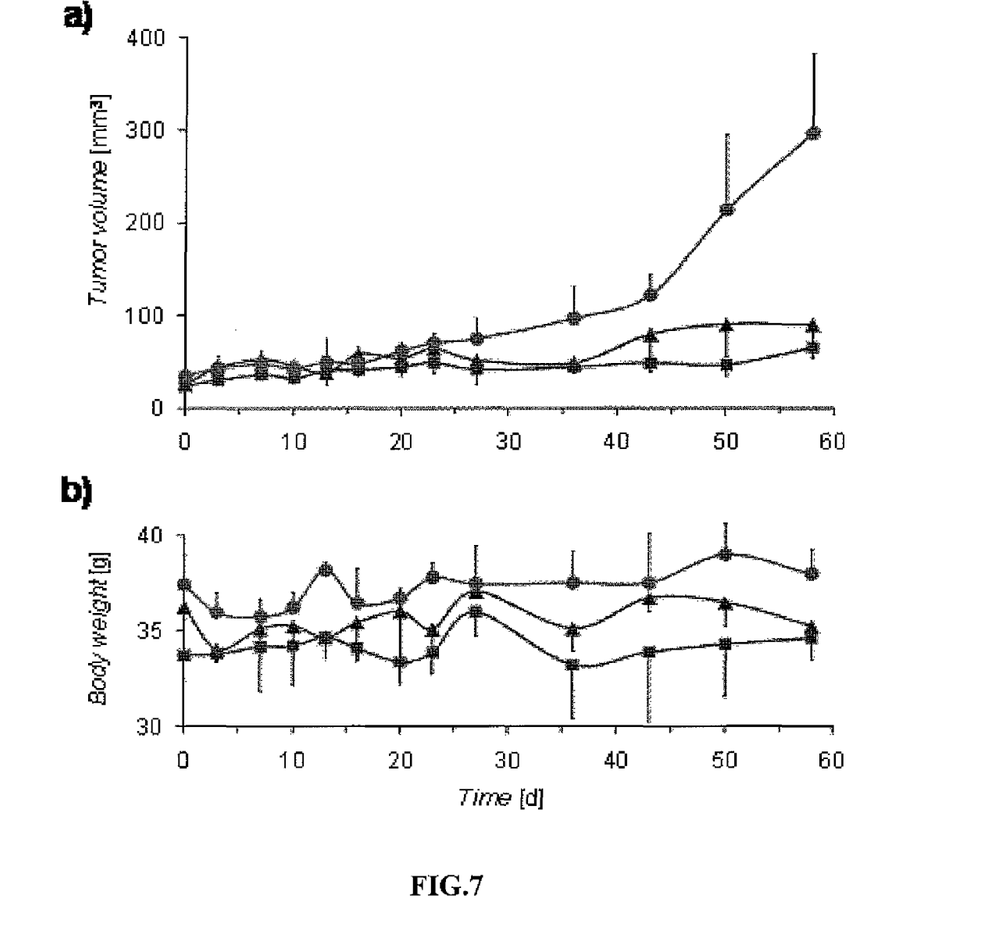
FIG. 7: Evolution of a) tumor volume and b) body weight over 8 weeks for mice injected with physiological serum (●), mice injected with Taxol® (▲) and mice injected with PDA-PEG2000 micelles loaded with paclitaxel (■).

These results, shown in FIG. 6, demonstrate that the behavior of PDA-PEG2000 micelles is perfectly suitable for therapeutic protocols involving multiple injections over an extended period of time. Further, results showed that the tumor growth was significantly decreased in the two groups of mice treated with Taxol® and micelles loaded with PTX (FIG. 7). After 2 months, the tumor volumes were reduced by an average factor of 3.3 for Taxol® and 4.5 for PTX-loaded micelles, in comparison to control mice injected with physiological serum. These results demonstrate the efficiency of the micelle for drug delivery.

Apart from the good distribution and accumulation observed, it should be noted that none of the involved animals died during the experiment, providing additional evidence of the innocuous nature of the cargo itself. Furthermore, body weights of the treated mice remained steady, indicating that PTX-loaded PDA-PEG2000 micelles were well tolerated.

4. Conclusion

PDA-PEG2000 micelles, the most promising nanoparticle presented here, have been studied further in order to determine their drug-loading ability and in vitro cytotoxicity. Obvious differences were observed between the different micelle types. It appeared that PEG350-coated micelles were superior to NTA-coated ones, but the benefit was far more significant with PEG2000-coated micelles. The latter particles demonstrated longer blood residence time, excellent tumor uptake and better imaging contrast.

In addition, PDA-PEG2000 micelles were easily and efficiently loaded with paclitaxel, showed good in vitro cytotoxicity and behaved ideally in multiple injection conditions. Moreover, no toxicity attributable to the carrier itself was observed throughout the different experiments that were carried out.

The combination of imaging and drug-loading properties in a single object points out PDA-PEG2000 micelles as potential tools for theragnosis, able to achieve simultaneous diagnosis and treatment, thus rendering the overall medical process less invasive and easier to carry out.

5. Experimental Section

Materials: Chemicals were purchased from Aldrich. Common organic solvents were used without further purification. Dichloromethane was distilled over $CaH_2$, tetrahydrofurane and diethyl ether over sodium/benzophenone prior to use. NMR spectra were recorded on a Bruker Advanced 400 at 400 MHz ($^1$H) and 100 MHz ($^{13}$C). Chemical shifts are given in ppm relative to the NMR solvent residual peak. Mass spectra were recorded using a Mariner™ ESI-TOF spectrometer. IR-spectra were recorded using a Perkin-Elmer 2000 FT-IR. Wavenumbers are given in cm$^{-1}$ at their maximum intensity. Size distributions of micelles were measured using a Zetasizer Nano series (Malvern).

Synthesis of pentacosa-10,12-diyn-1-ol (5): To a solution of penatcosa-10,12-diynoic acid (1 g–2.7 mmol–1 eq.) in diethyl ether (50 mL) cooled at 4° C. on an ice bath, lithium aluminium hydride (205 mg–5.4 mmol–2 eq.) was added under nitrogen atmosphere. After stirring for 1.5 h at room temperature, the reaction was cooled again to 4° C. and 15% sodium hydroxide (200 µL) was added, followed by water (600 µL). The resulting pink precipitate was filtered off on Celite® and the filtrate was washed with hydrochloric acid (2×20 mL) and dried on magnesium sulfate. After solvent removal under vacuum, product 5 was obtained as a white solid (938 mg–2.6 mmol–ρ=96%).

$^1$H NMR (400 MHz, CDCl$_3$, δ): 3.63 (t, J=7 Hz, 2H; CH$_2$—OH), 2.23 (t, J=7 Hz, 4H; CH$_2$—C≡), 1.60-1.45 (M, 6H; CH$_2$), 1.44-1.24 (M, 28H; CH$_2$), 0.86 ppm (t, J=7 Hz, 3H; CH$_3$); $^{13}$C NMR (100 MHz, CDCl$_3$, δ): 77.5 (—C≡), 77.4 (—C≡), 65.2 (—C≡), 65.2 (—C≡), 63.1 (CH$_2$—OH), 32.7 (CH$_2$), 31.9 (CH$_2$), 29.6 (3 CH$_2$), 29.4 (CH$_2$), 29.3 (3 CH$_2$), 29.1 (CH$_2$), 29.0 (CH$_2$), 28.8 (CH$_2$), 28.7 (CH$_2$), 28.3 (CH$_2$), 28.2 (2 CH$_2$), 25.7 (CH$_2$), 22.6 (CH$_2$), 19.2 (CH$_2$), 14.1 ppm (CH$_3$); IR (KBr): v=3411 (w), 3345 (m), 2955 (w), 2919 (s), 2850 (s), 1469 (m), 1061 (w), 717 cm$^{-1}$ (m); MS (ESI$^+$, m/z): 361 [M+H]$^+$ Synthesis of 1-bromopentacosa-10,12-diyne (6): Triphenylphosphine (550 mg–2.1 mmol–1.5 eq.) and 5 (500 mg–1.4 mmol–1 eq.) were solubilized in dichloromethane (3 mL) under nitrogen atmosphere. Tetrabromomethane (700 mg–2.1 mmol–1.5 eq.) was added in portions and the reaction was stirred at room temperature for 15 minutes. After addition of cold water (2 mL) the organic phase was separated, dried over magnesium sulfate and purified on a silica plug eluted with pure dichloromethane. Upon concentration under reduced pressure, the desired product 6 was obtained as a yellowish varnish (585 mg–1.38 mmol–ρ=100%).

$^1$H NMR (400 MHz, CDCl$_3$, δ): 3.40 (t, J=7 Hz, 2H; CH$_2$—Br), 2.24 (t, J=7 Hz, 4H; CH$_2$—C≡), 1.85 (td, J=7 Hz, 2H; CH$_2$), 1.60-1.45 (M, 6H; CH$_2$), 1.45-1.25 (M, 26H; CH$_2$), 0.88 ppm (t, J=7 Hz, 3H; CH$_3$); $^{13}$C NMR (100 MHz, CDCl$_3$, δ): 77.6 (—C≡), 77.4 (—C≡), 65.3 (—C≡), 65.1 (—C≡), 34.0 (CH$_2$—Br), 32.8 (CH$_2$), 31.9 (CH$_2$), 29.6 (3 CH$_2$), 29.4 (CH$_2$), 29.3 (CH$_2$), 29.2 (CH$_2$), 29.1 (2 CH$_2$), 28.9 (CH$_2$), 28.8 (CH$_2$), 28.7 (CH$_2$), 28.6 (CH$_2$), 28.3 (CH$_2$), 28.2 (CH$_2$), 28.1 (CH$_2$), 22.7 (CH$_2$), 19.2 (CH$_2$), 14.1 ppm (CH$_3$); IR (film): v=2926 (s), 2854 (s), 1465 (m), 1322 (w), 1261 (w), 722 (m), 672 cm$^{-1}$ (m); MS (ESI$^+$, m/z): 422 [M+H]$^+$ Synthesis of pentacosa-10,12-diyn-1-oxyoctaethyleneglycol (2a) and pentacosa-10,12-diyn-1-oxypentatetracontaethyleneglycol (2b): Poly(ethylene glycol) (PEG350: 350 mg–1 mmol–1 eq. or PEG2000: 2 g–1 mmol–1 eq.) dissolved in anhydrous acetonitrile (20 mL) was added to a suspension of sodium hydride (48 mg–2 mmol–2 eq.) in anhydrous acetonitrile (10 mL) under nitrogen. The mixture was refluxed for 30 minutes and allowed to cool down to room temperature. Compound 6 (422 mg–1 mmol–1 eq.) dissolved in tetrahydrofurane (5 mL) was slowly added and the reaction was stirred at room temperature for 96 hours. After concentration under vacuum, purification by column chromatography (silica gel, dichloromethane/methanol 95:5) yielded the desired product (2a: colorless solid—392 mg–0.55 mmol–$\rho$=55% or 2b: yellow solid—800 mg–0.4 mmol–$\rho$=40%).

2a: $^1$H NMR (400 MHz, CDCl$_3$, $\delta$): 3.62 (M, 32H; CH$_2$—O), 3.40 (t, J=7 Hz, 2H; CH$_2$—O), 2.21 (t, J=7 Hz, 4H; CH$_2$—C≡), 1.60-1.42 (M, 6H; CH$_2$), 1.40-1.25 (M, 28H; CH$_2$), 0.86 ppm (t, J=7 Hz, 3H; CH$_3$); $^{13}$C NMR (100 MHz, CDCl$_3$, $\delta$): 77.5 (—C≡), 77.2 (—C≡), 72.5 (CH$_2$—O), 71.5 (CH$_2$—O), 70.5 (12 CH$_2$—O), 70.3 (CH$_2$—O), 70.0 (CH$_2$—O), 65.2 (—C≡), 65.1 (—C≡), 61.7 (CH$_2$—OH), 31.9 (CH$_2$), 29.6 (4 CH$_2$), 29.4 (3 CH$_2$), 29.3 (CH$_2$), 29.2 (CH$_2$), 29.1 (CH$_2$), 29.0 (CH$_2$), 28.9 (CH$_2$), 28.8 (CH$_2$), 28.3 (2 CH$_2$), 26.1 (CH$_2$), 22.6 (CH$_2$), 19.2 (CH$_2$), 14.1 ppm (CH$_3$); IR (KBr): v=3489 (w), 2932 (s), 2888 (s), 2850 (s), 1463 (m), 1354 (m), 1343 (m), 1276 (m), 1136 (m), 1112 (s), 1062 (m), 967 (m), 941 (m), 846 (m), 720 cm$^{-1}$ (w); MS (ESI$^+$, m/z): 713 [M+H]$^+$ 2b: $^1$H NMR (400 MHz, CDCl$_3$, $\delta$): 3.65 (M, 180H; CH$_2$—O), 3.42 (t, J=7 Hz, 2H; CH$_2$—O), 2.22 (t, J=7 Hz, 4H; CH$_2$—C≡), 1.60-1.45 (M, 6H; CH$_2$), 1.35-1.20 (M, 28H; CH$_2$), 0.88 ppm (t, J=7 Hz, 3H; CH$_3$); $^{13}$C NMR (100 MHz, CDCl$_3$, $\delta$): 77.4 (—C≡), 77.3 (—C≡), 72.4 (CH$_2$—O), 71.4 (CH$_2$—O), 70.5 (86 CH$_2$—O), 70.2 (CH$_2$—O), 69.9 (CH$_2$—O), 65.3 (—C≡), 65.2 (—C≡), 61.5 (CH$_2$—OH), 31.8 (CH$_2$), 29.5 (4 CH$_2$), 29.4 (CH$_2$), 29.3 (3 CH$_2$), 29.2 (2 CH$_2$), 29.0 (CH$_2$), 28.9 (CH$_2$), 28.7 (CH$_2$), 28.2 (2 CH$_2$), 25.9 (CH$_2$), 22.6 (CH$_2$), 19.1 (CH$_2$), 14.0 ppm (CH$_3$); IR (KBr): v=3497 (w), 2922 (s), 2884 (s), 2860 (s), 1467 (m), 1360 (m), 1345 (m), 1280 (m), 1148 (m), 1113 (s), 1061 (m), 964 (m), 946 (m), 843 (m), 724 cm$^{-1}$ (w); MS (ESI$^+$, m/z): 2343 [M+H]$^+$ Synthesis of carboxylic-terminated derivatives 3a and 3b: pentacosa-10,12-diyn-1-oxypoly(ethylene glycol) (2a: 145 mg–0.2 mmol–1 eq. or 2b: 468 mg–0.2 mmol–1 eq.) dissolved in tetarhydrofurane (5 mL) was added to a suspension of sodium hydride (12 mg–0.5 mmol–2.5 eq.) in tetrahydrofurane (5 mL) under nitrogen. The mixture was refluxed for 30 minutes and allowed to cool down to room temperature. 2-bromoacetic acid (195 mg–1.4 mmol–7 eq.) dissolved in tetrahydrofurane (2 mL) was slowly added and the reaction was stirred at room temperature for 24 hours. After concentration under vacuum, purification by column chromatography (silica gel, dichloromethane/methanol 95:5) yielded the desired product (3a: colorless varnish— 133 mg–0.17 mmol–$\rho$□=86% or 3b: yellow varnish—384 mg–0.16 mmol–$\rho$=80%).

3a: $^1$H NMR (400 MHz, CDCl$_3$, $\delta$): 3.83 (s, 2H, O—CH$_2$—CO$_2$H), 3.70-3.60 (M, 32H; CH$_2$—O), 3.42 (t, J=7 Hz, 2H; CH$_2$—O), 2.20 (t, J=7 Hz, 4H; CH$_2$—C≡), 1.60-1.45 (M, 6H; CH$_2$), 1.40-1.20 (M, 28H; CH$_2$), 0.85 ppm (t, J=7 Hz, 3H; CH$_3$); $^{13}$C NMR (100 MHz, CDCl$_3$, $\delta$): 168.8 (CO$_2$H), 77.5 (—C≡), 77.2 (—C≡), 72.4 (CH$_2$—O), 71.5 (CH$_2$—O), 70.5 (12 CH$_2$—O), 70.1 (CH$_2$—O), 70.0 (CH$_2$—O), 68.7 (O—CH$_2$—CO$_2$H), 65.2 (—C≡), 65.1 (—C≡), 61.5 (CH$_2$—O), 31.8 (CH$_2$), 29.6 (3 CH$_2$), 29.5 (CH$_2$), 29.4 (CH$_2$), 29.3 (2 CH$_2$), 29.2 (CH$_2$), 29.1 (CH$_2$), 29.0 (CH$_2$), 28.8 (2 CH$_2$), 28.7 (CH$_2$), 28.3 (2 CH$_2$), 26.1 (CH$_2$), 22.6 (CH$_2$), 19.2 (CH$_2$), 14.1 ppm (CH$_3$); IR (film): v=3480 (m), 2925 (m), 2855 (s), 1738 (m), 1465 (m), 1349 (m), 1285 (m), 1251 (m), 1111 (s), 1041 (m), 950 (m), 848 (m), 722 cm$^{-1}$ (w); MS (ESI$^+$, m/z): 771 [M+H]$^+$ 3b: $^1$H NMR (400 MHz, CDCl$_3$, $\delta$): 3.90 (s, 2H, O—CH$_2$—CO$_2$H), 3.80-3.60 (M, 180H; CH$_2$—O), 3.51 (t, J=7 Hz, 2H; CH$_2$—O), 2.24 (t, J=7 Hz, 4H; CH$_2$—C≡), 1.65-1.47 (M, 6H; CH$_2$), 1.40-1.25 (M, 28H; CH$_2$), 0.88 ppm (t, J=7 Hz, 3H-1; CH$_3$); $^{13}$C NMR (100 MHz, CDCl$_3$, $\delta$): 169.1 (CO$_2$H), 77.5 (—C≡), 77.3 (—C≡), 72.4 (CH$_2$—O), 71.6 (CH$_2$—O), 70.6 (86 CH$_2$—O), 70.1 (CH$_2$—O), 70.0 (CH$_2$—O), 68.6 (O—CH$_2$—CO$_2$H), 65.2 (—C≡), 65.1 (—C≡), 61.6 (CH$_2$—O), 31.6 (CH$_2$), 29.6 (3 CH$_2$), 29.5 (CH$_2$), 29.4 (CH$_2$), 29.3 (2 CH$_2$), 29.2 (CH$_2$), 29.1 (CH$_2$), 29.0 (CH$_2$), 28.8 (2 CH$_2$), 28.7 (CH$_2$), 28.2 (2 CH$_2$), 26.2 (CH$_2$), 22.6 (CH$_2$), 19.2 (CH$_2$), 14.0 ppm (CH$_3$); IR (film): v=3486 (m), 2915 (s), 2853 (s), 1723 (m), 1463 (m), 1339 (in), 1279 (m), 1256 (m), 1114 (s), 1045 (m), 953 (m), 841 (m), 720 cm$^{-1}$ (w); MS (ESI$^+$, m/z): 2401 [M+H]$^+$ Preparation of polymerized micelles: A solution of compound 1 (50 mg) in 0.01 M aqueous sodium hydroxide (5 mL) was sonicated with an ultrasonic probe (Output 4, DutyCycle 30%) for 10 minutes. The solution was then submitted to UV light (254 nm–low pressure mercury UV lamp–Heraeus) irradiation for 6 hours to yield PDA-NTA micelles. Hydrochloric acid was added until pH 7 was reached.

For the assembly of PDA-PEG micelles, compounds 2 (25 mg) and 3 (25 mg) were dissolved in deionized water (5 mL) yielding a solution that underwent a protocol identical to that described for PDA-NTA micelles (though no pH adjustment was needed for these micelles).

Preparation of Fluorescent Micelles: To a solution of micelles (either PDA-PEG2000, PDA-PEG350 or PDA-NTA micelles) into PBS buffer was added EDC (10 equiv.) and the reaction was stirred for 30 minutes at RT. Then, NHS-sulfo (10 equiv.) was added and the reaction was stirred for 10 minutes, and finally the fluorochrome FP730 amino (10 equiv) was added. The reaction mixture was stirred overnight and then purified over an exclusion gel column (Sephadex G-25: NAP-10 from GE Healthcare or Bio-Spin column from Bio-Radad) by centrifugation. The purification process was repeated until no more FP730 remains on the column. The process was checked by UV absorbance.

Preparation of samples for in vivo experiments: The injected solution was made by diluting micelles grafted with FP730 and unfunctionnalized micelles with PBS buffer in order to have a final concentration of 5 µM for FP730 and 2.5 mM for the monomer unit of the considered micelles. A volume of 200 µL is injected.

Animal experiments: All procedures were in accordance with international guidelines on the ethical use of animals. All mice that were used were female nude mice weighting approximately 23 g and housed under standard conditions with food and water ad libitum.

Implantation of cancer cells: For each mouse implanted, a syringe was prepared containing 10$^6$ tumor cells MDA-MB231 in a volume of 100 µL of PBS mixed with 100 µL of Matrigel™ at 0° C. For PC12-MEN2A cells, 3 10$^6$ cells were directly diluted into 200 µL of PBS.

All cancer cells were subcutaneously implanted into the neck of mice and let grow until the desired tumor size was reach.

Biodistribution by Fluorescence imaging: To a group of at least 3 mice having been inoculated with cancer cells (PC12-MEN2A or MDA-MB231) a solution of fluorescent micelles (previously described) was intravenously injected in their tail under isoflurane anesthesia. Always under anesthesia, a planar fluorescent picture of each mouse's backside and frontside was taken before and after the iv injection using a 3D optical tomography apparatus developed by CEA/LETI and Cyberstar. Planar pictures were taken at various time points (1 min, 10 min, 30 min, 1 h, 3 h, 6 h, 1 day and every following day over a week) and 3D scans were done on the tumor zone before injection and every day after over a week.

Injected nanoparticles were: PDA-PEG2000-FP730 micelles, PDA-PEG350-FP730 micelles, PDA-NTA-FP730 micelles, fluorochrome FP730 alone and a non covalent mixture of PDA-PEG2000 micelles and FP730 to be in the same concentration condition as the sample PDA-PEG2000-FP730 micelles.

For semiquantitative analysis of fluorescence images round ROIs of the desired zone (tumor and legs) were selected manually by using the ImageJ software. Each ROI's value was corrected by substracting the background ROI's value (same zone but before injection) and dividing it by the exposure time. Another correction was also applied taking into account the quenching of the fluorochrome overtime: 18% in 7 days. To calculate this value a sealed capillary containing a known concentration of FP730 was put into a phantom mimicking a mouse. The phantom was put in the very same process condition and pictures were taken for the same time points.

PET-FDG/fDOT multimodal imaging: [$^{18}$F]-FDG (Flucis®, Cis Bio International) [7.4 MBq, (200 µCi)] was injected in the tail vein of mice previously injected with PDA-PEG2000-FP730 micelles 24 h before. Then the anaesthetized animals were immediately positioned on a custom made multi-modality mouse supporting plate that allows co-registration between PET- and fDOT-acquired data, and a dynamic PETscan was acquired for 90 min with a microPET Focus 220 scanner system (Siemens-Concorde Microsystems). The mouse supporting plate was thereafter transported and positioned in the fDOT apparatus scanner and 3D scans were done on the tumor zone.

For PET imaging, image acquisitions (Focus 220 MicroPET seamier) and reconstructions were done using the MicroPET Manager software (Siemens-Concorde Microsystems). PET images were reconstructed with the following frame durations: 5×1 min, 5×2 min, 5×3 min. The dimensions of reconstruction volumes were 256×256×95×[number of time frames] with a voxel size of 0.475×0.475×0.796 mm$^3$. The output signal units were given in Bq/cc. fDOT reconstructions were performed as described in the Biodistribution by Fluorescence imaging section.

Co-registration and analysis of images from fDOT and PET were performed using a user-friendly, in-house toolbox that is integrated within the Brainvisa medical imaging processing software (http://brainvisa.info/index_f.html).[17]

Blood clearance kinetics: Blood samples were collected from the retro-orbital venous sinus using heparin coated capillary tubes before and after the intravenous administration of the fluorescent nanoparticles. Three mice were used for each type of micelles and samples (~30 µL) were collected at various time points (after 1 min, 5 min, 10 min, 30 min, 1 h, 2 h, 3 h and 24 h). Just after blood retrieval, the latter was centrifuge for 5 min at 1000×g into an eppendorf tube in order to retrieve the plasma that contained all the fluorescence. The fluorescence was measured by analyzing the plasma into a capillary tube (so height and depth could be reproducible) with an optical tomography apparatus developed by Cyberstar and the CEA/LETI. The acquisition time was of 400 ms. For semiquantitative analysis of fluorescence images square ROIs of the capillaries were selected manually by using the ImageJ software.

Micelle metabolism: Plasma samples (the same as the ones used for blood clearance kinetics) were used in order to evaluate the metabolism of the injected nanoparticles. The collected samples were deposited into a 3% agarose gel (without ethidium bromide) and run over 20 minutes at 100 W. The samples were compared respectively to the same nanoparticle either in a PBS buffer and mixed with pure plasma just before the run.

Agarose gels were analyzed with an optical apparatus (Cyberstar, CEA/LETI). The acquisition time was of 400 ms. For semiquantitative analysis of fluorescence images the ImageJ software was used.

Drug loading of PDA-PEG2000 micelles: A stock solution of compounds 2b (15 mg) and 3b (15 mg) in deionized water (3 mL) is divided in three equal parts. Paclitaxel (25 mg) is added to two of these (solution A and solution B), and the last (solution C) is left without any additive. All three solutions/suspensions are sonicated with an ultrasonic probe (Output 4, DutyCycle 30%) for 10 minutes. The solutions/suspensions are then submitted to UV light (254 nm–low pressure mercury UV lamp–Heraeus) irradiation for 6 hours and filtrated on 0.22 µm membranes to remove insoluble drug aggregates. The loading of paclitaxel ($L_{PTX}$) in PDA-PEG2000 micelles was quantified by freeze-drying the filtrates of solutions B and C and comparing the masses ($m_B$ and $m_C$) of the obtained solid residues ($L_{PTX}=[m_B-m_C]/m_B$). The filtrate of solution A is used for further experiments.

In vitro cell proliferation assay: In a 96 well plate were deposited 2 10$^3$ cells (MDA-MB231) diluted in 50 µL of culture medium. After 24 h in a cell incubator, 50 82 L of a solution of Taxol® at different paclitaxel concentrations (250, 120, 60, 40, 30, 20, 10, 5, 2, 1, and 0.5 µM) in a PBS buffer was added. Each concentration was repeated 3 times. The plate was then allowed to stand in a cell incubator for 48 h. Then, 20 µL of MTS (tetrazolium compound included in the CellTiter 96® AQ$_{ueous}$ Non-Radioactive Cell Proliferation Assay) were added and the plate was analyzed with a Mithras microplate reader (LB 940, Berthold) at 490 nm after 2 hours of incubation in a cell incubator.

The data were compared to well containing only 2 10$^3$ cells in 50 µL of culture medium and 50 µL of PBS buffer and revealed with 20 µL of MTS. To all data a background was removed consisting of 50 µL of culture medium and 50 µL of PBS buffer and revealed with 20 µL of MTS.

The same procedure was followed using a solution of PDA-PEG2000-PTX micelles at different paclitaxel concentrations (500, 250, 160, 140, 120, 100, 80, 60, 40, 30, 20, 10, 5, 2, 1, and 0.5 µM).

The plot was expressed as a function of a percentage of living cells, 100% being the well containing only cells and MTS.

Repeated injection of PDA-PEG2000-FP730 micelles: Over 5 weeks, a group of 3 mice were injected intravenously repeatedly, twice a week, with a solution of PDA-PEG2000-FP730 micelles (as described previously). Planar images were taken using the 3D optical tomographic system at various time points (before injection, after 1, 2, 3, 6, 7, 8, 9, 10, 13, 14, 15, 16, 17, 20, 23, 27, 28, and 30 days).

For semiquantitative analysis of fluorescence images the ImageJ software was used.

REFERENCES

[1] A.-C. Faure, S. Dufort, V. Josserand, P. Perriat, J.-L. Coll, S. Roux, O. Tillement, *Small* 2009, 5, 2565.

[2] E. K. U. Larsen, T. Nielsen, T. Wittenborn, H. Birkedal, T. Vorup-Jensen, M. H. Jakobsen, L. Østergaard, M. R. Horsman, F. Besenbacher, K. A. Howard, J. Kjems, *ACS Nano* 2009, 3, 1947.

[3] J.-H. Lee, K. Lee, S. H. Moon, Y. Lee, T. G. Park, J. Cheon, *Angew. Chem. Int. Ed.* 2009, 48, 4174.

[4] L.-Y. Tang, Y.-C. Wang, Y. Li, J.-Z. Du, J. Wang, *Bioconjugate Chem.* 2009, 20, 1095.

[5] W. Wei, G.-H. Ma, G. Hu, D. Yu, T. Mcleish, Z.-G. Su, Z.-Y. Shen, *J. Am. Chem. Soc.* 2008, 130, 15808.

[6] S. Dhara, F. X. Gub, R. Langerb, O. C. Farokhzadc, S. J. Lippard, *Proc. Natl. Acad. Sci. USA* 2008, 105, 17356.

[7] J. Gao, K. Chen, R. Xie, J. Xie, S. Lee, Z. Cheng, X. Peng, X. Chen, *Small* 2010, 6, 256.

[8] Z. Yang, S. Zheng, W. J. Harrison, J. Harder, X. Wen, J. G. Gelovani, A. Qiao, C. Li, *Biomacromolecules* 2007, 8, 3422.

[9] V. Ntziachristos, C. Bremer, R. Weissleder, *Eur. Radiol.* 2003, 13, 195; V. Ntziachristos, J. Ripoll, R. Weissleder, *Opt. Lett.* 2002, 27, 527.

[10] K. E. Adams, S. Ke, S. Kwon, F. Liang, Z. Fan, Y. Lu, K. Hirschi, M. E. Mawad, M. A. Barry, E. M. Sevick-Muraca, *J. Biomed. Opt.* 2007, 12, 024017.

[11] D. Peer, Jeffrey M. Karp, S. Hong, O. C. Farokhzad, R. Margalit, R. Langer, *Nature Nanotechnology* 2007, 2, 751.

[12] A. Pluen, Y. Boucher, S. Ramanujan, T. D. McKee, T. Gohongi, E. di Tomaso, E. B. Brown, Y. Izumi, R. B. Campbell, D. A. Berk, R. K. Jain, *Proc. Natl. Acad. Sci. USA* 2001, 98, 4628.

[13] V. P. Torchilin, *Pharm. Res.* 2007, 24, 1.

[13a] T. Lammers, W. E. Hennink, G. Storm, *Br. J. Cancer* 2008, 99, 392.

[13b] J. Ogier, T. Arnauld, E. Doris, *Future Med. Chem.* 2009, 1, 693.

[13c] S. D. Perrault, C. Walkey, T. Jennings, H. C. Fischer, W. C. Chan, *Nano Lett.* 2009, 9, 1909.

[13d] A. Pluen, Y. Boucher, S. Ramanujan, T. D. McKee, T. Gohongi, E. di Tomaso, E. B. Brown, Y. Izumi, R. B. Campbell, D. A. Berk, R. K. Jain, *Proc. Natl. Acad. Sci. USA*. 2001, 98, 4628.

[14] Z. Zhang, J. Chen, L. Ding, H. Jin, J. F. Lovell, I. R. Corbin, W. Cao, P.-C. Lo, M. Yang, M.-S. Tsao, Q. Luo, G. Zheng, *Small* 2010, 6, 430.

[14a] H. Sixl, C. Kollmar, R. Huber, E. Sigmund, *Phys. Rev. B* 1987, 36, 2747.

[14b] C. Kollmar, *J. Chem. Phys.* 1993, 98, 7210.

[14c] C. Itoh, T. Kondoh, K. Tanimura, *J. Phys. Soc. Jpn.* 1999, 68, 1711.

[14d] Y. Okawa, M. Aono, *J. Chem. Phys.* 2001, 115, 2317.

[15] D. E. Owens 3rd, N. A. Peppas, *Int. J. Pharm.* 2006, 307, 93.

[16] J. Ogier, T. Arnauld, G. Carrot, A. Lhumeau, J. M. Delbos, C. Boursier, O. Loreau, F. Lefoulon, E. Doris. *Org. Biomol. Chem.,* 2010, DOI: 10.1039/C004134C

[17] A. Garofalakis, A. Dubois, B. Kuhnast, D. M. Dupont, I. Janssens, N. Mackiewicz, F. Dolle, B. Tavitian, F. Duconge, *Opt. Lett.* 2010, 35, 3024.

The invention claimed is:

1. A method of in vivo diagnosis comprising: administering an effective amount of a polymerized micelle comprising:
   a diagnostic agent; and
   an amphiphilic polymer obtainable by the polymerization of an amphiphilic monomer, the monomer comprising a hydrophilic head comprising a polyoxyethylene chain;

wherein:
the polymerized micelle has a hydrodynamic diameter of less than 30 nm; and
the amphiphilic monomer is of formula (I):

wherein:
X is $-(CH_2-CH_2-O)_n-Z$;
Y is $-C\equiv C-C\equiv C-$;
$L_0$ is a bond;
$L_1$ is $-(CH_2)_p-$;
$L_2$ is $-(CH_2)_q-CH_3$;
Z is H, or $-CH_2-COOH$;
n is an integer from 5 to 230;
k is an integer from 1 to 5;
p is at each occurrence an integer from 1 to 24; and
q is an integer from 1 to 24.

2. The method of claim 1, wherein the diagnostic agent is cancer diagnostic agent.

3. The method of claim 2, wherein the diagnostic agent is a fluorescent compound.

4. The method of claim 2, wherein the diagnostic agent is either coupled with a hydrophilic head or loaded in the micelle.

5. The method of claim 1, wherein n is 8 or 45.

6. The method of claim 1, wherein the amphiphilic polymer is obtained by the polymerization of a mixture comprising a first amphiphilic monomer wherein Z is H and a second amphiphilic monomer of formula (I) wherein Z is $-CH_2-COOH$.

7. The method of claim 6, wherein the amphiphilic polymer further comprises a targeting entity.

8. The method of claim 7, wherein the targeting entity is an aptamer.

9. A polymerized micelle comprising: an amphiphilic polymer obtainable by the polymerization of an amphiphilic monomer of formula (I):

wherein:
X is $-(CH_2-CH_2-O)-Z$;
Y is $-C\equiv C-C\equiv C-$;
$L_0$ is a bond;
$L_1$ is $-(CH_2)_p-$;
$L_2$ is $-(CH_2)_q-CH_3$;
Z is H or $-CH_2-COOH$;
n is an integer from 5 to 230;
k is an integer from 1 to 5;
p is at each occurrence an integer from 1 to 24; and
q is an integer from 1 to 24;
and wherein the polymerized micelle has a hydrodynamic diameter of less than 30 nm.

10. The polymerized micelle of claim 9, wherein a group Z of the polymerized micelle is coupled to a diagnostic agent.

11. A method of preparing a polymerized micelle of claim 9, the method comprising:
   i) self-assembling the amphiphilic monomer of formula (I) into micelles; and
   ii) polymerizing self-assembled micelles obtained in step i).

12. A diagnostic composition comprising a polymerized micelle of claim 9.

13. The method of claim 11, further comprising coupling a Z group of the obtained polymerized micelle with a diagnostic agent.

14. The composition of claim 12, further comprising a pharmaceutically acceptable excipient.

15. The polymerized micelle of claim 10, wherein the diagnostic agent is a substance emitting electromagnetic rays or a substance detectable by X-ray, ultrasound or nuclear magnetic resonance.

16. The method of claim 1, wherein $L_0$ is a bond.

* * * * *